(12) United States Patent
Moreau-Gobard

(10) Patent No.: US 7,920,731 B2
(45) Date of Patent: Apr. 5, 2011

(54) BLEEDING DETECTION USING A BLANKET ULTRASOUND DEVICE

(75) Inventor: Romain Moreau-Gobard, Palo Alto, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 628 days.

(21) Appl. No.: 12/051,034

(22) Filed: Mar. 19, 2008

(65) Prior Publication Data

US 2009/0003675 A1 Jan. 1, 2009

Related U.S. Application Data

(60) Provisional application No. 60/908,272, filed on Mar. 27, 2007.

(51) Int. Cl.
*G06K 9/00* (2006.01)

(52) U.S. Cl. ....................................................... 382/128

(58) Field of Classification Search .................. 382/128, 382/131, 132, 154; 600/443–447, 454; 601/2
See application file for complete search history.

(56) References Cited

U.S. PATENT DOCUMENTS

| | | |
|---|---|---|
| 5,882,302 A | 3/1999 | Driscoll, Jr. et al. |
| 5,993,389 A | 11/1999 | Driscoll, Jr. et al. |
| 6,083,159 A | 7/2000 | Driscoll, Jr. et al. |
| 6,503,202 B1 * | 1/2003 | Hossack et al. ............... 600/454 |
| 6,626,855 B1 | 9/2003 | Weng et al. |
| 6,719,694 B2 | 4/2004 | Weng et al. |
| 7,063,666 B2 | 6/2006 | Weng et al. |
| 7,532,748 B2 * | 5/2009 | Lara-Montalvo et al. .... 382/131 |
| 2007/0066897 A1 | 3/2007 | Sekins et al. |
| 2007/0194658 A1 | 8/2007 | Zhang et al. |
| 2008/0312562 A1 * | 12/2008 | Routh et al. ...................... 601/2 |

* cited by examiner

*Primary Examiner* — Vu Le
*Assistant Examiner* — Claire Wang
(74) *Attorney, Agent, or Firm* — Donald B. Paschburg; F. Chau & Associates, LLC

(57) ABSTRACT

A method for differentiating between a blood vessel bifurcation and a bleeding blood vessel in an ultrasound volume includes performing vessel segmentation on the ultrasound volume, calculating vessel centerlines for the segmented vessels, automatically detecting a bifurcation candidate using the calculated vessel centerlines, placing a first marker at a predetermined distance before the detected bifurcation candidate, placing a second marker at a predetermined distance after the bifurcation candidate, placing a third marker at a predetermined distance alone a potential vessel branch of the bifurcation candidate, acquiring spectral Doppler waveform data at each of the three markers, and comparing the acquired spectral Doppler waveform data for each of the three markers to determine whether the bifurcation candidate is a point of internal bleeding.

20 Claims, 9 Drawing Sheets

BLEEDING DETECTION USING A BLANKET ULTRASOUND DEVICE

CROSS-REFERENCE TO RELATED APPLICATION

The present application is based on provisional application Ser. No. 60/908,272, filed Mar. 27, 2007, the entire contents of which are herein incorporated by reference.

BACKGROUND OF THE INVENTION

1. Technical Field

The present disclosure relates to bleeding detection and, more specifically, to bleeding detection in blanket ultrasound device.

2. Discussion of Related Art

Ultrasound devices have long been used as a safe and effective means for visualizing the internal structure of a patient. Unlike visualization using x-rays, ultrasound does not expose the patient to potentially harmful ionizing radiation. Modern advances in ultrasound imaging technology have allowed for increased image clarity and enhanced resolution. Accordingly, ultrasound is a particularly interesting branch of medical imaging technology.

However, medical imaging techniques such as ultrasound have traditionally required the use of imaging equipment that can be both large and heavy. Thus, medical imaging is generally confined to hospitals and other clinical facilities. There are times, however, when patients requiring medical attention cannot obtain timely access to appropriate medical facilities. For example, solders on the battlefield, researches in remote locations, astronauts on the International Space Station and those engaged in the sport of traversing dangerous terrain may sustain life-threatening injury without access to appropriate medical facilities.

Of particular concern is the health of military personnel who sustain traumatic injury to the extremities. Such injuries are increasingly common as modern body armor including ballistic vests provides a high level of protection to the torso while leaving the arms and legs vulnerable. Such injuries may result in internal bleeding of the blood vessels, an injury that can quickly become fatal if not stabilized in a timely fashion.

Accordingly, efforts have been directed towards developing an imaging device that is portable, light-weight and flexible and capable of detecting and stabilizing injuries of the extremities such as internal bleeding of blood vessels of the arms and legs. One such class of devices utilizes a cuff or blanket, including multiple ultrasound transducers, for wrapping around the injured arm or leg. Such a device may be called an "ultrasound blanket" and may be small and light weight enough to be carried for use in emergency situations.

The ultrasound blanket may use multiple ultrasound transducers to locate an area requiring medical attention and may then be able to administer appropriate treatment, for example, using a high intensity focused ultrasound (HIFU) beam to focus energy at a particular location within the patient's body to cauterize an internally bleeding blood vessel.

At this time ultrasound blankets are still under development as many of the technical hurdles necessary to implement the ultrasound blanket have not yet been overcome. One such technical hurdle relates to the localization of bleeding blood vessels within an injured extremity. If a location of internal bleeding can be precisely identified then the bleeding can be effectively treated.

SUMMARY

A method for locating internal bleeding of a blood vessel includes acquiring a plurality of image subvolume data sets from a plurality of ultrasound transducers, combining the plurality of image subvolume data sets to form a combined image volume, performing vessel segmentation on the combined image volume, automatically detecting one or more bifurcation candidates, acquiring spectral Doppler waveform data at each of the detected one or more bifurcation candidates, and determining whether the one or more bifurcation candidates are points of internal bleeding based on the acquired spectral Doppler waveform data.

The set of ultrasound transducers may be incorporated into an ultrasound blanket or cuff. Combining the plurality of image subvolume data sets may include matching structures visible in the image volume data sets. Vessel segmentation may be performed using 3D power Doppler image data. The automatic detection of bifurcation candidates may include calculating vessel centerlines for the segmented vessels.

The step of acquiring spectral Doppler waveform data at each of the detected one or more bifurcation candidates may include placing a first marker at a predetermined distance before the detected bifurcation candidate, placing a second marker at a predetermined distance after the bifurcation candidate, placing a third marker at a predetermined distance alone a potential vessel branch of the bifurcation candidate, and acquiring spectral Doppler waveform data at each of the three markers.

The step of acquiring spectral Doppler waveform data at each of the three markers may include determining one or more acquisition planes that are most suitable for acquiring spectral Doppler waveform data at each of the three markers and acquiring the spectral Doppler waveform data at each of the three markers using the determined acquisition planes.

Determining the one or more acquisition planes that are most suitable for acquiring spectral Doppler waveforms may include finding an acquisition plane that is substantially co-liner with a segment of the vessel at the respective marker.

The step of determining whether the one or more bifurcation candidates are points of internal bleeding may include comparing the acquired spectral Doppler waveform data for each of the three markers. It may be determined that the one or more bifurcation candidates are points of internal bleeding when one or more of the acquired spectral Doppler waveform data for the three markers indicate an abnormal blood flow. It may be determined that the one or more bifurcation candidates are actual bifurcations when none of the acquired spectral Doppler waveform data for the three markers indicate an abnormal blood flow.

The plurality of ultrasound transducers may acquire image subvolumes from different angles and positions.

A method for differentiating between a blood vessel bifurcation and a bleeding blood vessel in an ultrasound volume includes performing vessel segmentation on the ultrasound volume, calculating vessel centerlines for the segmented vessels, automatically detecting a bifurcation candidate using the calculated vessel centerlines, placing a first marker at a predetermined distance before the detected bifurcation candidate, placing a second marker at a predetermined distance after the bifurcation candidate, placing a third marker at a predetermined distance alone a potential vessel branch of the bifurcation candidate, acquiring spectral Doppler waveform data at each of the three markers, and comparing the acquired spectral Doppler waveform data for each of the three markers to determine whether the bifurcation candidate is a point of internal bleeding.

The ultrasound image may be generated by combining a plurality of image subvolume data sets acquired from a plurality of ultrasound transducers arranged in an ultrasound blanket or cuff. Vessel segmentation may be performed using 3D power Doppler image data.

The step of acquiring spectral Doppler waveform data at each of the three markers may include determining one or more acquisition planes that are most suitable for acquiring spectral Doppler waveform data at each of the three markers and acquiring the spectral Doppler waveform data at each of the three markers using the determined acquisition planes.

Determining the one or more acquisition planes that are most suitable for acquiring spectral Doppler waveforms may include finding an acquisition plane that is substantially co-liner with a segment of the vessel at the respective marker.

A computer system includes a processor and a program storage device readable by the computer system, embodying a program of instructions executable by the processor to perform method steps for locating internal bleeding of a blood vessel. The method includes acquiring a plurality of image subvolume data sets from a plurality of ultrasound transducers incorporated into an ultrasound blanket or cuff, combining the plurality of image subvolume data sets to form a combined image volume, performing vessel segmentation on the combined image volume, automatically detecting a bifurcation candidate, acquiring spectral Doppler waveform data at the detected bifurcation candidate, and determining whether the bifurcation candidate is a point of internal bleeding based on the acquired spectral Doppler waveform data.

The step of acquiring spectral Doppler waveform data at the detected bifurcation candidate may include placing a first marker at a predetermined distance before the detected bifurcation candidate, placing a second marker at a predetermined distance after the bifurcation candidate, placing a third marker at a predetermined distance alone a potential vessel branch of the bifurcation candidate, and acquiring spectral Doppler waveform data at each of the three markers.

It may be determined that the bifurcation candidate is a point of internal bleeding when one or more of the acquired spectral Doppler waveform data for the three markers indicate an abnormal blood flow.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
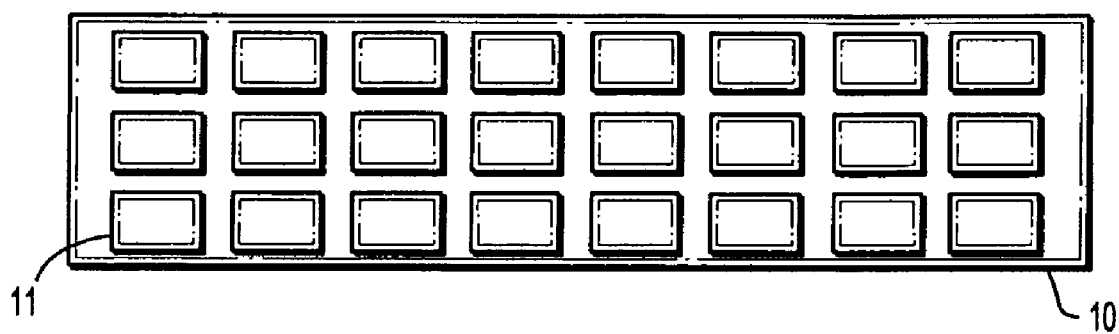
FIG. 1 is a schematic diagram illustrating a portion of an ultrasound blanket according to an exemplary embodiment of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide an approach for detecting and precisely locating internal bleeding using a set of ultrasound transducers such as may be found in an ultrasound blanket.

FIG. 1 is a schematic diagram illustrating a portion of an ultrasound blanket according to an exemplary embodiment of the present invention. The illustrated portion of the ultrasound blanket 10 includes a plurality of ultrasound transducers 11. The transducers 11 may be arranged in rows and columns, as shown, or may be staggered. The ultrasound blanket 10 may be rigid or flexible. Where the ultrasound blanket 10 is rigid, each transducer 11 may be articulated so that it may be free to move in one or more directions.

Figure 2:
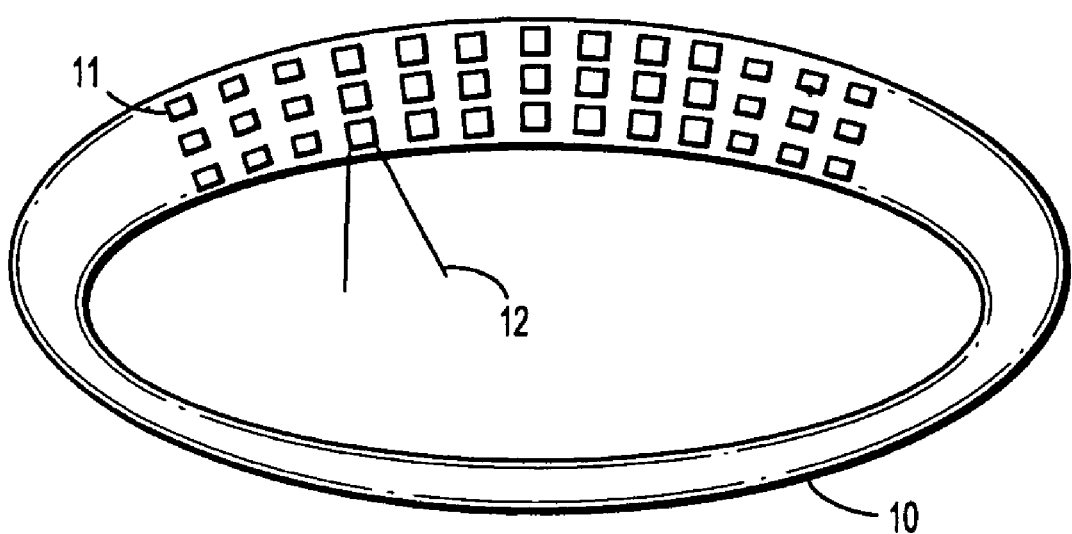
FIG. 2 is a perspective view of an ultrasound blanket shaped as a cuff according to an exemplary embodiment of the present invention.

The ultrasound blanket 10 may be shaped as a cuff to facilitate placement around an extremity of a patient. FIG. 2 is a perspective view of an ultrasound blanket shaped as a cuff according to an exemplary embodiment of the present invention. Here the ultrasound blanket 10 may be formed in a ring shape that may be either short or long. For example the ultrasound blanket 10 may be long enough to cover a large portion of a patient's leg. Ultrasound transducers 11 may be provided to cover the entire surface of the ultrasound blanket 10. For example, the ultrasound transducers 11 may be provided to completely encircle an extremity of a patient.

Each ultrasound transducer 11 may be equipped to provide multiple modalities, for example, each transducer 11 may be able to collect 3D B-mode data, be able to collect power Doppler data, be able to collect spectral Doppler data, and/or may be able to provide an HIFU beam. In collecting ultrasound data in accordance with one of the above-named modalities, or other such modalities, each transducer may be able to obtain image data corresponding to a conic volume 12. The conic volumes of the multiple transducers 11 may overlap at parts and thus a single point of the subject may be captured by many different transducers from many different angles.

Figure 3:
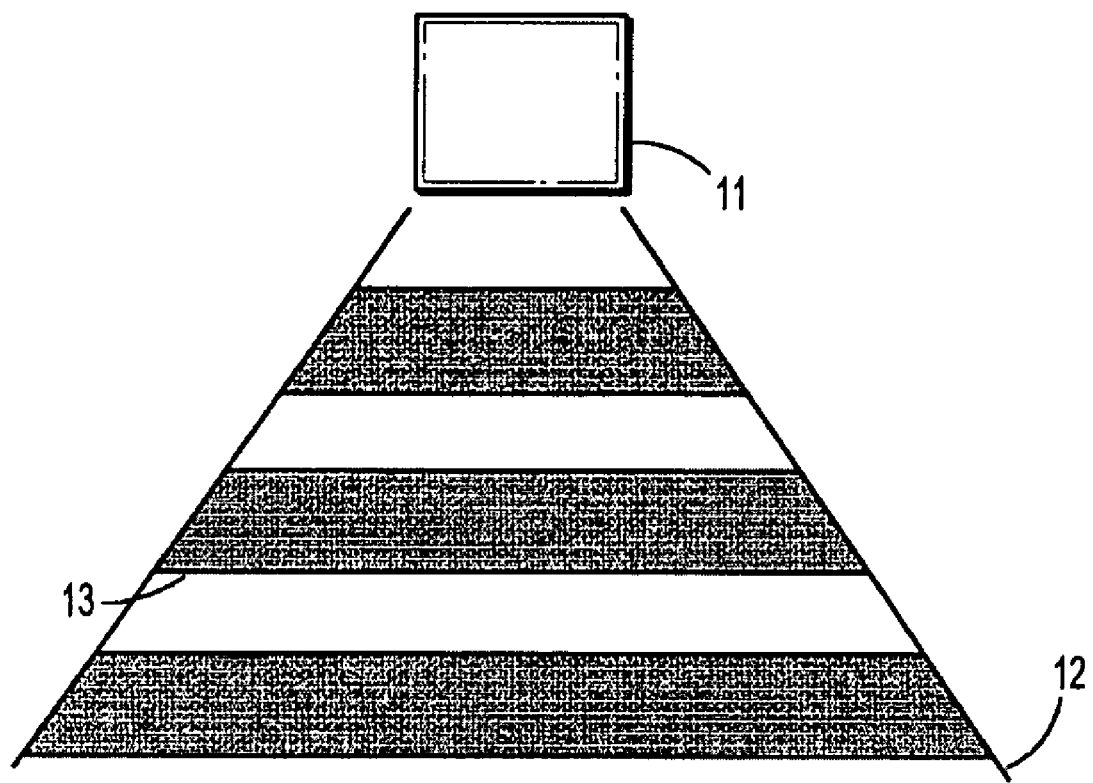
FIG. 3 is a schematic diagram illustrating an ultrasound transducer and its corresponding imaging field according to an exemplary embodiment of the present invention.

FIG. 3 is a schematic diagram illustrating an ultrasound transducer and its corresponding imaging field according to an exemplary embodiment of the present invention. As described above, each transducer 11 may be able to image a volume within a cone 12. The captured image data may include multiple planes 13. Each plane is a two-dimensional image slice of the image volume. A single point of the subject may be imaged by multiple image planes of multiple image volumes.

As described above, the ultrasound blanket may include a collection of ultrasound transducers or tiles aligned in a flexible structure that may be wrapped around an injured area of a patient. Each transducer may individually perform ultrasound imaging to generate a localized set of image data. Each localized set of image data may be a three-dimensional image volume. The multiple image volumes may be overlapping and a particular point within the patient's body may be imaged by multiple transducers from multiple angles. Because ultrasound waves may not pass through dense tissue such as bone and ultrasound images may include certain artifacts that may prevent accurate imaging from certain angles, it is likely that certain internal structures may be better imaged from certain angles. Thus, exemplary embodiments of the present invention seek to combine the multiple sets of image data obtained from the multiple ultrasound transducers to build a highly detailed and accurate combined view of the internal structure being examined and then identify, within the combined view, a location of internal bleeding.

Figure 4:
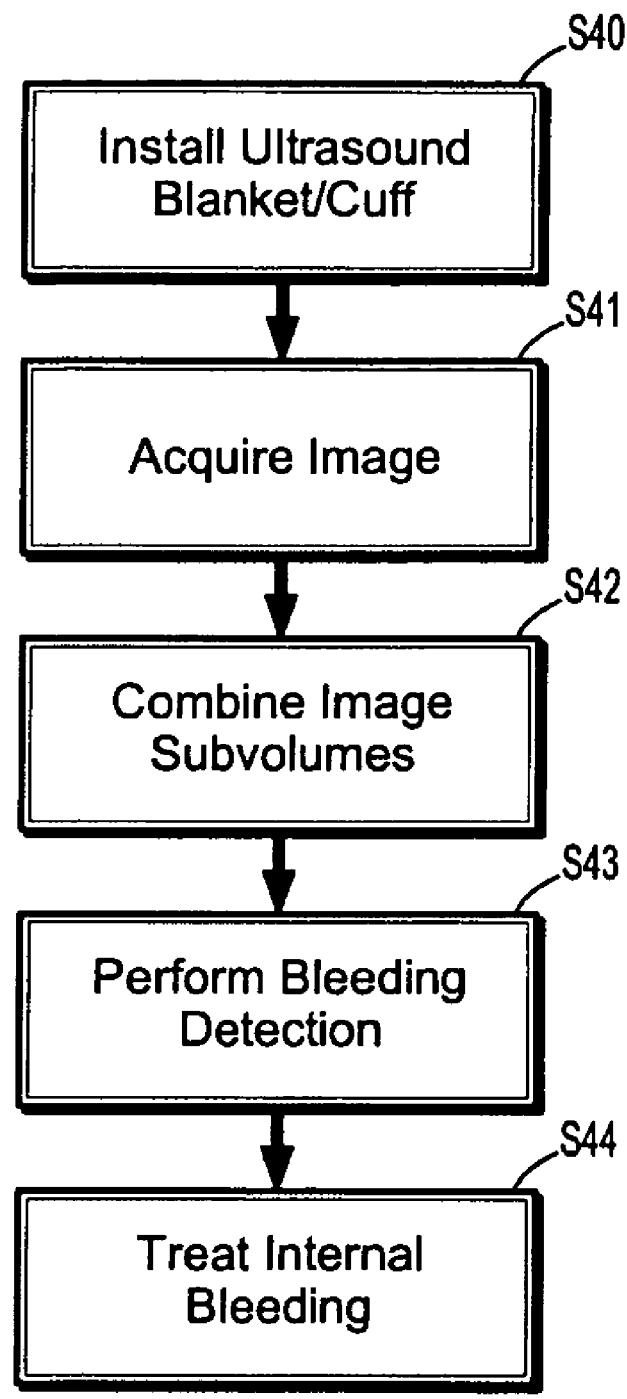
FIG. 4 is a flowchart illustrating a method for treating internal bleeding using an ultrasound blanket according to an exemplary embodiment of the present invention.

FIG. 4 is a flowchart illustrating a method for treating internal bleeding using an ultrasound blanket according to an exemplary embodiment of the present invention. However, as a preliminary matter, the ultrasound blanket/cuff may be installed around the site of injury (Step S40). This may include, for example, placing a cuff-shaped ultrasound blanket around the patient's injured arm or leg. Next, image acquisition may commence (Step S41). In image acquisition, each ultrasound transducer of the ultrasound blanket may obtain an image data set representing a localized volume. Each volume may be cone-shaped as described above. The many ultrasound transducers may operate simultaneously, taking into account, the ultrasonic waves generated by the other transducers and the way in which they may interfere, or may function one after the other. Image acquisition may include one or more ultrasound modalities, for example, 3D B-Mode image data and 3D power Doppler image data may be collected.

After the multiple image volumes have been obtained, the multiple image volumes may be combined to form a single image volume (Step S42). Having a single combined image volume may provide spatially-coherent information such as is seen in CT or MRI datasets. In forming the combined image volume, data pertaining to the known configuration of the multiple ultrasound may be used. Additionally or alternatively, the multiple image volumes may be combined by matching structures visible in multiple image volumes.

The multiple image volumes may at least partially overlap such that structural data of a particular point may be covered by more than one image volume. The combined image volumes may utilize image data that shows a particular structure with the greatest clarity and least obstruction. Moreover, the volumetric compounding of the multiple image data sets, taken from multiple angles, may significantly increase the quality of the combined image volume. In combining the image volumes, known techniques for multiple image stitching may be used. For example, the many volumes may be co-registered according to features present in the volume images. Volume stitching may be performed automatically or may utilize user input.

Next, bleeding detection may be performed on the combined image volume (Step S43). In this step, the precise location of the bleeding may be pinpointed in three-dimensional space. The bleeding may be internal bleeding originating from a blood vessel that has sustained an injury. Methods for detection of bleeding are described in detail below with reference to FIG. 5. Finally, therapy may be directed to the precise location of the bleeding to effectively contain the bleeding and stabilize the patient (Step S44). As discussed above, this may include the use of an HIFU beam, focused directly to the site of the bleeding to cauterize the bleeding vessel.

Figure 5:
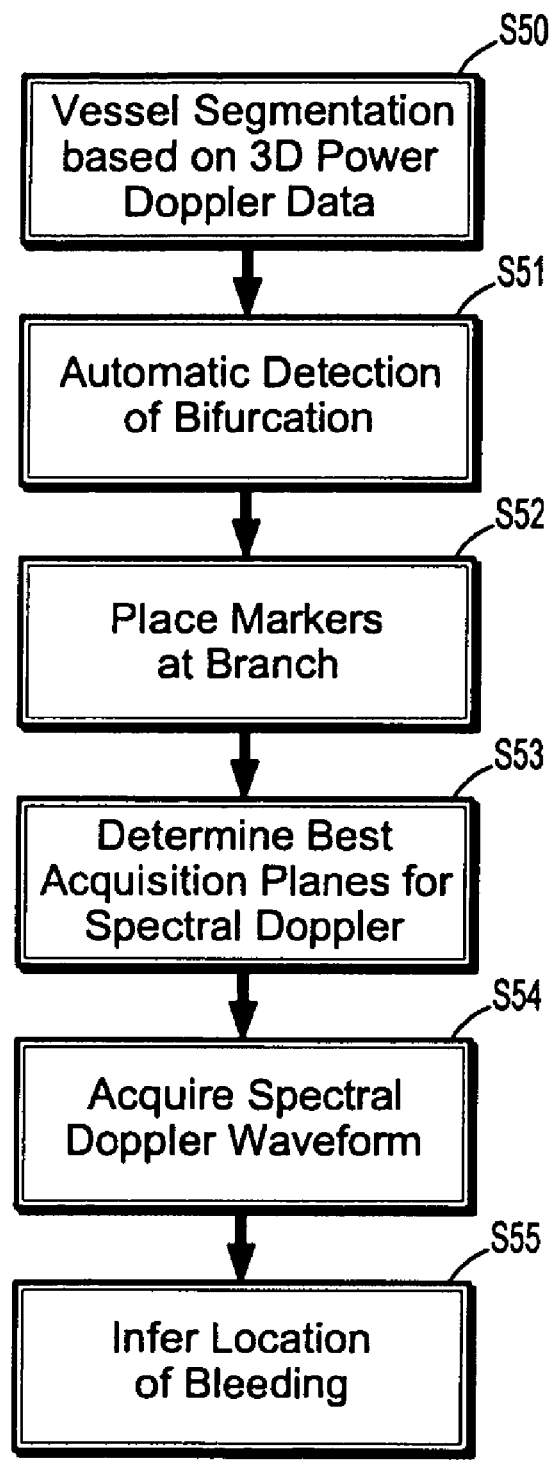
FIG. 5 is a flowchart illustrating a method for detecting internal bleeding originating from a blood vessel according to an exemplary embodiment of the present invention.

FIG. 5 is a flowchart illustrating a method for detecting the location of a bleeding vessel within the combined image volume using an ultrasound blanket according to an exemplary embodiment of the present invention. This process is briefly discussed above with respect to Step S43, however, additional detail relating to performing this step are provided below with respect to exemplary embodiments of the present invention.

First, vessel segmentation may be performed (Step S50). Segmentation may be performed, for example, using three-dimensional intensity data known as 3D B-mode data. In the 3D B-Mode, the brightness of each voxel is based on the intensity of the echo return. In color flow images, the movement of fluid such as blood may be illustrated by the use of different colors. This may be accomplished by examining the frequency shift of backscattered ultrasound waves. The change or shift in backscatter frequency increases as blood flows towards the transducer and decreases as blood flows away from the transducer. In color flow imaging, this Doppler shift is represented using different colors which indicates the velocity of blood flow. Similarly, in Power Doppler imaging, the power contained in the returned Doppler signal is displayed.

Power Doppler image data may also be used, for example, in combination with the 3D-B mode data to perform segmentation, as a blood vessel may be visible from the power Doppler image data and/or the 3D-B mode data.

Segmentation may be used to provide a binary mask that characterizes the shape of the blood vessels. For example, where voxels that are not part of a blood vessel are assigned a value of 0 and voxels that are part of a blood vessel are assigned a value of 1.

As segmentation may be performed on the combined image, known techniques for 3D image segmentation may be perfumed.

After segmentation has been performed, automatic detection of vessel bifurcation may be performed (Step S51). Automatic detection of vessel bifurcation may result in the identification of places along a vessel where branching occurs. This step may include calculating a vessel centerline from the segmented image data. The vessel centerline may be calculated, for example, using a thinning algorithm. In a thinning algorithm, a structure is transformed into a line without degrading the continuity of the structure by sequentially removing pixels from opposite ends of the structure in the width direction. In a sense, the width is removed layer by layer until all that is left is a thin centerline that represents the continuity of the stricture. In one exemplary embodiment of the present invention, the 3D Power Doppler data that indicates fluid movement may be used to detect the branching. The branching information may then be combined with the vessel centerline information so that each bifurcation may be detected at the centerline.

Figure 6:
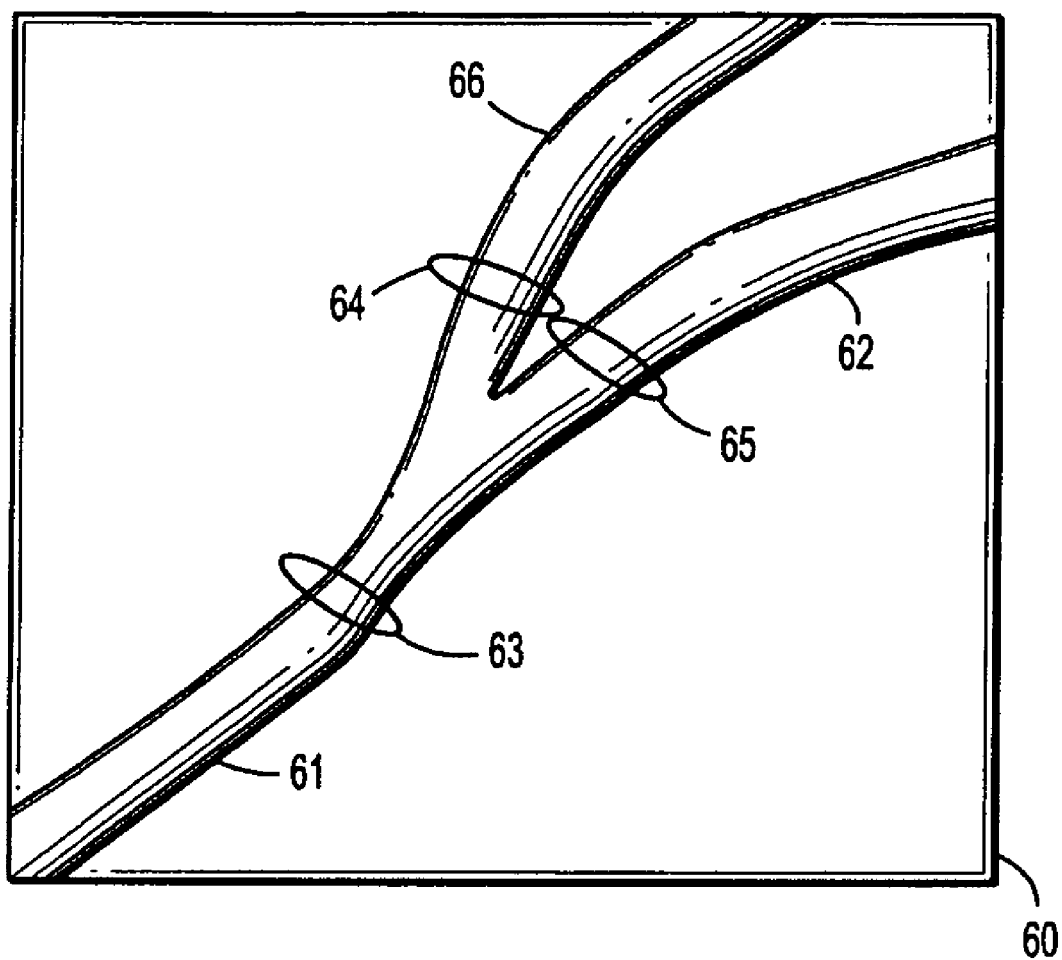
FIG. 6 is a diagram illustrating a bifurcated blood vessel that is marked for spectral Doppler acquisition according to an exemplary embodiment of the present invention.

Markers may then be placed before and after each bifurcation (Step S52). FIG. 6 is a diagram 60 illustrating a bifurcated blood vessel 61 that is marked according to an exemplary embodiment of the present invention. In total there may be three markers, one marker 63 indicating a region on the vessel 61 a set distance before the bifurcation. A second marker 65 may indicate a region on the vessel a set distance after the bifurcation 62. A third marker 64 may indicate a region on the vessel branch a set distance after the bifurcation 66.

Next, it may be determined which acquisition planes of which transducers are best equipped for acquiring a spectral Doppler modality (Step S53). As discussed above, each transducer is capable of imaging a particular local volume and each local volume may include a set of 2D acquisition planes. Selecting an appropriate acquisition plane for performing spectral Doppler imaging may include determining which transducer has the clearest access to and/or the best angle with respect to the vessel or vessel section that is to be imaged with the spectral Doppler modality. For example, the best acquisition plane may be the acquisition plane of a transducer that has a clear view of the vessel or vessel segment to be imaged and where the acquisition plane is substantially co-linear with the vessel segment.

Figure 7:
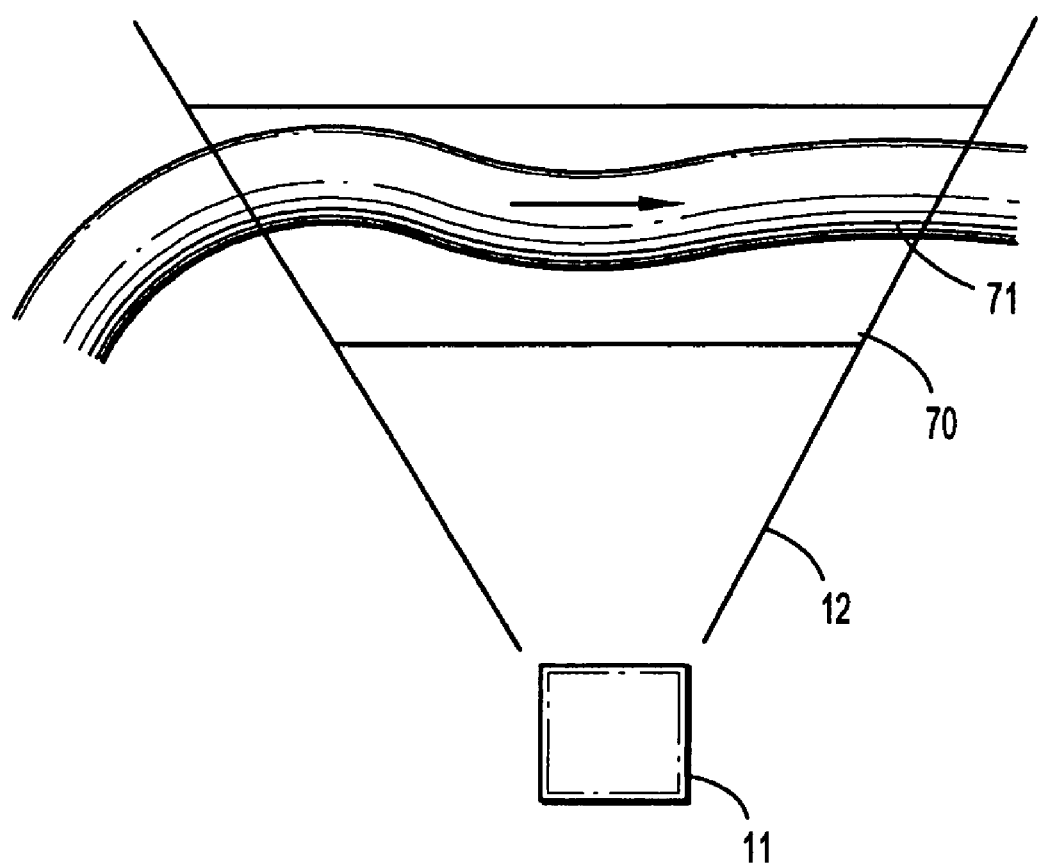
FIG. 7 is a schematic illustrating a best acquisition plane for imaging a vessel segment according to an exemplary embodiment of the present invention.

FIG. 7 is a schematic illustrating a best acquisition plane for imaging a vessel segment according to an exemplary embodiment of the present invention. Here, a suitable acquisition plane 70 for performing spectral Doppler imaging of a vessel segment 71 is within an image volume 12 of a transducer 11. The suitable acquisition plane 70 is shown as being substantially co-linear with respect to the vessel segment 71.

After the best acquisition plane is selected, a spectral Doppler waveform may be acquired using the selected transducer at the selected acquisition plane (Step S54). The ultrasound modality of spectral Doppler may be used to determine the flow characteristics at the regions of interest. Here, spectral Doppler waveform data may be acquired at each of the three marked locations along the vessel as discussed above and illustrated in FIG. 6. By examining the flow characteristics at the locations before the bifurcation, after the bifurcation and along the vessel branch, the presence of abnormal flow conditions may be detected.

When imaging the vessel structure using ultrasound transducers, for example, as discussed above, it may be difficult to accurately distinguish between a bleeding vessel and a bifurcated vessel. Accordingly, spectral Doppler waveform data may be acquired for all bifurcation candidates at each of the three above described locations to differentiate between a true bifurcation and a bleeding vessel. Thus in the final step the location of a bleeding vessel may be inferred by determining that a bifurcation candidate is in fact a bleeding vessel (Step S55).

Figure 8:
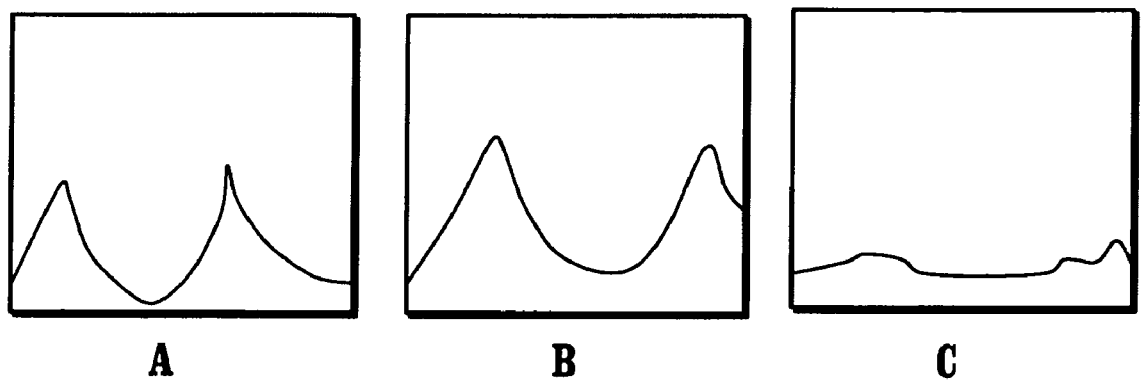
FIGS. 8A-C illustrate three exemplary spectral Doppler waveforms acquired at the position of a bifurcation candidate according to an exemplary embodiment of the present invention.

FIGS. 8A-C illustrate three exemplary spectral Doppler waveforms acquired at the position of a bifurcation candidate according to an exemplary embodiment of the present invention. FIG. 8A represents a spectral Doppler waveform acquired at a position before the bifurcation candidate. FIG. 8B represents a spectral Doppler waveform acquired at a position after the bifurcation candidate. FIG. 8C represents a spectral Doppler waveform acquired at a position along the bifurcation candidate. In cases where the bifurcation candidate is a true bifurcation, each of the three spectral Doppler waveforms should appear similar as the flow of blood through non-bleeding vessels would appear regular and normal at each of the three marked positions. However, where the bifurcation candidate is not a true bifurcation but is actually a bleeding vessel, the spectral Doppler waveform of at one of the three marked positions may appear abnormal, as is illustrated in FIG. 8C.

Accordingly, the use of spectral Doppler waveform data at each of the three marked positions along the bifurcation candidate can differentiate between a true bifurcation and a bleeding vessel. By performing this check at each identified bifurcation candidate of a patient's extremity under test, the presence of bleeding blood vessels may be identified and precisely located.

The methods described above may be implemented using a computer system. The computer system may be integrated with the ultrasound blanket/cuff device or may be in communication with the device. The computer system may be a centralized computer system embodied in one location or may be a distributed computer system with a separate computing device incorporated into each ultrasound transducer.

Figure 9:
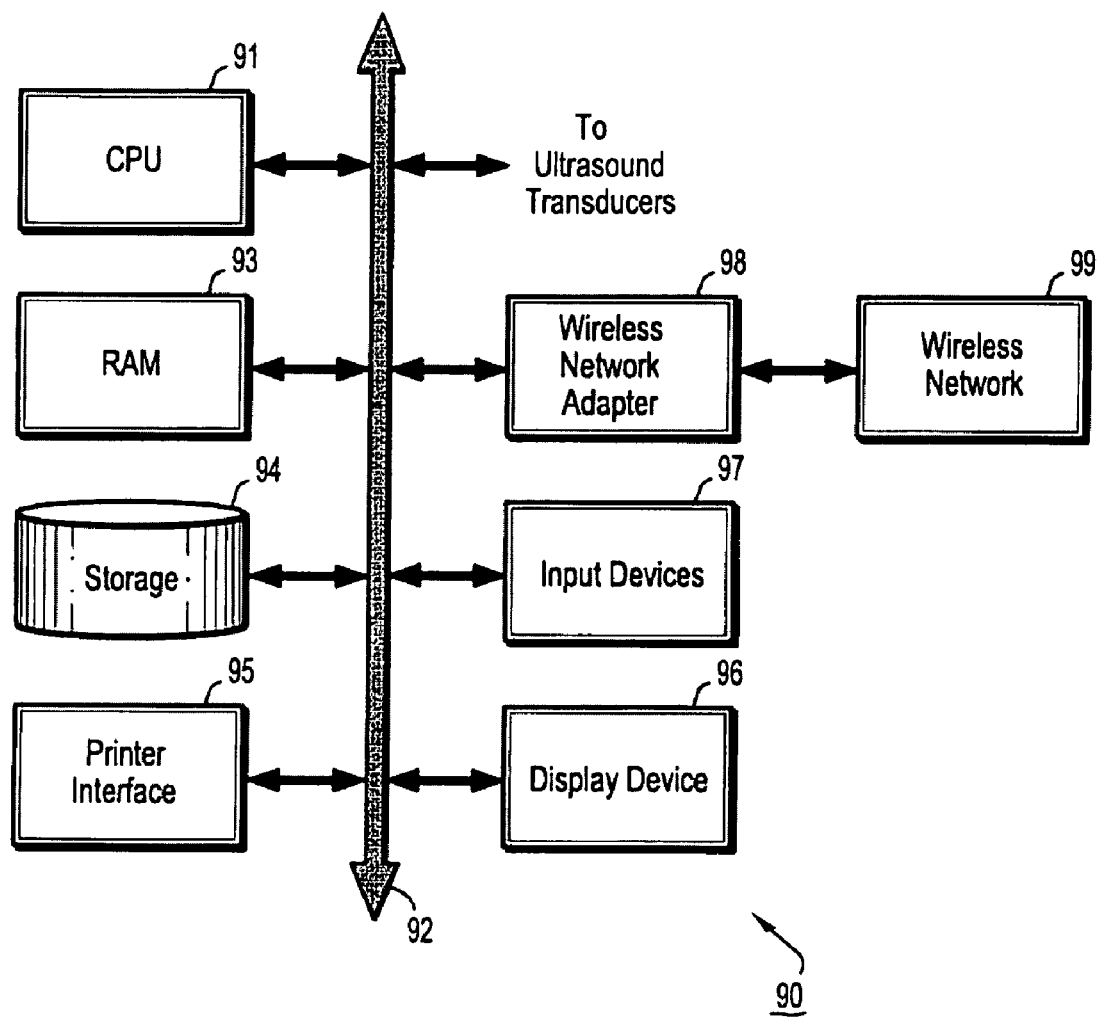
FIG. 9 shows an example of a computer system capable of implementing the method and apparatus according to embodiments of the present disclosure.

FIG. 9 shows an example of a computer system which may implement a method and system of the present disclosure. The system and method of the present disclosure may be implemented in the form of a software application running on a computer system, for example, a portable personal computer (PC), for example, a laptop PC, a handheld computer, for example, a PDA, or a special-purpose embedded computer. The software application may be stored on a recording media or firmware locally accessible by the computer system.

The computer system 80 may include, for example, one or more central processing units (CPU) 81, random access memory (RAM) 83, a storage device 84 such as a hard disk drive (HDD) or a solid state disk (SSD), a printer interface 85 for connecting the computer system 80 to a printing device, a display device 86, for example, an LCD display, one or more input devices 87 for receiving user commands such as a keypad and/or a pointing device, a wireless network adapter 88 such as a cellular modem, a WiFi and/or WiMAX network adapter, a satellite modem, etc. The wireless network adapter 88 may provide access to a wireless computer network 89 over which data may be transmitted and/or received. The various components of the computer system 80 may communicate with each other over one or more data buses 82. The plurality of ultrasound transducers may be in communication with the computer system 80, for example, through the one or more data buses 82 or though an interface device connected thereto.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for locating internal bleeding of a blood vessel, comprising:
    acquiring a plurality of image subvolume data sets from a plurality of ultrasound transducers;
    combining the plurality of image subvolume data sets to form a combined image volume;
    performing vessel segmentation on the combined image volume;
    automatically detecting one or more bifurcation candidates;
    acquiring spectral Doppler waveform data at each of the detected one or more bifurcation candidates; and
    determining whether the one or more bifurcation candidates are points of internal bleeding based on the acquired spectral Doppler waveform data.

2. The method of claim 1, wherein the set of ultrasound transducers is incorporated into an ultrasound blanket or cuff.

3. The method of claim 1, wherein combining the plurality of image subvolume data sets includes matching structures visible in the image volume data sets.

4. The method of claim 1, wherein vessel segmentation is performed using 3D power Doppler image data.

5. The method of claim 1, wherein the automatic detection of bifurcation candidates includes calculating vessel centerlines for the segmented vessels.

6. The method of claim 1, wherein the step of acquiring spectral Doppler waveform data at each of the detected one or more bifurcation candidates includes placing a first marker at a predetermined distance before the detected bifurcation candidate, placing a second marker at a predetermined distance after the bifurcation candidate, placing a third marker at a predetermined distance alone a potential vessel branch of the bifurcation candidate, and acquiring spectral Doppler waveform data at each of the three markers.

7. The method of claim 6, wherein the step of acquiring spectral Doppler waveform data at each of the three markers includes determining one or more acquisition planes that are most suitable for acquiring spectral Doppler waveform data at each of the three markers and acquiring the spectral Doppler waveform data at each of the three markers using the determined acquisition planes.

8. The method of claim 7, wherein determining the one or more acquisition planes that are most suitable for acquiring spectral Doppler waveforms includes finding an acquisition plane that is substantially co-liner with a segment of the vessel at the respective marker.

9. The method of claim 6, wherein the step of determining whether the one or more bifurcation candidates are points of internal bleeding includes comparing the acquired spectral Doppler waveform data for each of the three markers.

10. The method of claim 9, wherein it is determined that the one or more bifurcation candidates are points of internal bleeding when one or more of the acquired spectral Doppler waveform data for the three markers indicate an abnormal blood flow.

11. The method of claim 9, wherein it is determined that the one or more bifurcation candidates are actual bifurcations when none of the acquired spectral Doppler waveform data for the three markers indicate an abnormal blood flow.

12. The method of claim 1, wherein the plurality of ultrasound transducers acquire image subvolumes from different angles and positions.

13. A method for differentiating between a blood vessel bifurcation and a bleeding blood vessel in an ultrasound volume, comprising:
   performing vessel segmentation on the ultrasound volume;
   calculating vessel centerlines for the segmented vessels;
   automatically detecting a bifurcation candidate using the calculated vessel centerlines;
   placing a first marker at a predetermined distance before the detected bifurcation candidate;
   placing a second marker at a predetermined distance after the bifurcation candidate;
   placing a third marker at a predetermined distance alone a potential vessel branch of the bifurcation candidate;
   acquiring spectral Doppler waveform data at each of the three markers; and
   comparing the acquired spectral Doppler waveform data for each of the three markers to determine whether the bifurcation candidate is a point of internal bleeding.

14. The method of claim 13, wherein the ultrasound image is generated by combining a plurality of image subvolume data sets acquired from a plurality of ultrasound transducers arranged in an ultrasound blanket or cuff.

15. The method of claim 13, wherein vessel segmentation is performed using 3D power Doppler image data.

16. The method of claim 13, wherein the step of acquiring spectral Doppler waveform data at each of the three markers includes determining one or more acquisition planes that are most suitable for acquiring spectral Doppler waveform data at each of the three markers and acquiring the spectral Doppler waveform data at each of the three markers using the determined acquisition planes.

17. The method of claim 16, wherein determining the one or more acquisition planes that are most suitable for acquiring spectral Doppler waveforms includes finding an acquisition plane that is substantially co-liner with a segment of the vessel at the respective marker.

18. A computer system comprising:
   a processor; and
   a program storage device readable by the computer system, embodying a program of instructions executable by the processor to perform method steps for locating internal bleeding of a blood vessel, the method comprising:
   acquiring a plurality of image subvolume data sets from a plurality of ultrasound transducers incorporated into an ultrasound blanket or cuff;
   combining the plurality of image subvolume data sets to form a combined image volume;
   performing vessel segmentation on the combined image volume;
   automatically detecting a bifurcation candidate;
   acquiring spectral Doppler waveform data at the detected bifurcation candidate; and
   determining whether the bifurcation candidate is a point of internal bleeding based on the acquired spectral Doppler waveform data.

19. The computer system of claim 18, wherein the step of acquiring spectral Doppler waveform data at the detected bifurcation candidate includes placing a first marker at a predetermined distance before the detected bifurcation candidate, placing a second marker at a predetermined distance after the bifurcation candidate, placing a third marker at a predetermined distance alone a potential vessel branch of the bifurcation candidate, and acquiring spectral Doppler waveform data at each of the three markers.

20. The computer system of claim 18, wherein it is determined that the bifurcation candidate is a point of internal bleeding when one or more of the acquired spectral Doppler waveform data for the three markers indicate an abnormal blood flow.

* * * * *